(12) United States Patent
Lee et al.

(10) Patent No.: US 9,180,199 B2
(45) Date of Patent: Nov. 10, 2015

(54) POLYPEPTIDE BASED BLOCK COPOLYMER AND THE PROCESS FOR THE PREPARATION THEREOF, AND THE POLYMER MICELLES USING THE SAME

(71) Applicant: RESEARCH & BUSINESS FOUNDATION SUNGKYUNKWAN UNIVERSITY, Suwon-si (KR)

(72) Inventors: Doo Sung Lee, Suwon-si (KR); Yi Li, Suwon-si (KR); Bong Sup Kim, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 14/022,356

(22) Filed: Sep. 10, 2013

(65) Prior Publication Data

US 2014/0080922 A1  Mar. 20, 2014

(30) Foreign Application Priority Data

Sep. 10, 2012 (KR) ........................ 10-2012-0100072

(51) Int. Cl.
*A61K 47/42* (2006.01)
*A61K 47/34* (2006.01)
*A61K 9/107* (2006.01)

(52) U.S. Cl.
CPC ............... *A61K 47/42* (2013.01); *A61K 9/1075* (2013.01); *A61K 47/34* (2013.01)

(58) Field of Classification Search
None
See application file for complete search history.

(56) References Cited

FOREIGN PATENT DOCUMENTS

KR    10-2010-0112491 A    10/2010

OTHER PUBLICATIONS

Tian et al (Biomaterials (2005) 36: 4209-4217).*
Korean Office Action issued Aug. 25, 2014 in counterpart Korean Patent Application No. 10-2012-0100072 (4 pages, in Korean).
Carlsen, Autumn, and Sébastien Lecommandoux. "Self-assembly of polypeptides-based block copolymer amphiphiles." *Current Opinion in Colloid & Interface Science* 14 (2009) pp. 329-339.

* cited by examiner

*Primary Examiner* — Karlheinz R Skowronek
*Assistant Examiner* — Mindy Newman
(74) *Attorney, Agent, or Firm* — NSIP Law

(57) ABSTRACT

A polypeptide based block copolymer having biodegradability due to peptidase, a process for the preparation thereof, and polymer micelles using the same are provided. The block copolymer is a block copolymer of a polyethylene glycol-based compound having properties such that the solubility for water is different depending on the pH, but cannot form micelles due to a self-assembly phenomenon; and a polyglutamic acid-based compound formed using an aminolysis reaction of glutamic acid and tertiary amine in which the end of one alkyl group is substituted with $NH_2$, or using an aminolysis reaction of glutamic acid and triamine.

11 Claims, 7 Drawing Sheets

POLYPEPTIDE BASED BLOCK COPOLYMER AND THE PROCESS FOR THE PREPARATION THEREOF, AND THE POLYMER MICELLES USING THE SAME

STATEMENT REGARDING GOVERNMENT RIGHTS

This invention was made with government support of the Republic of Korea under Contract No. 2010-0027955 funded by the Ministry of Science, ICT, and Future Planning and the Basic Science Research Program through the National Research Foundation of Korea which is funded by the Ministry of Education (2013R1A1A2063367). The government has certain rights in the invention.

CROSS-REFERENCE TO RELATED APPLICATIONS

This application claims the benefit under 35 USC 119(a) of Korean Patent Application No. 10-2012-0100072 filed on Sep. 10, 2012, in the Korean Intellectual Property Office, the entire disclosure of which is incorporated herein by reference for all purposes.

BACKGROUND

1. Field

The present disclosure relates to a polypeptide based block copolymer having biodegradability due to peptidase, and a process for the preparation thereof, and polymer micelles using the same.

2. Description of Related Art

Micelles generally refer to a thermostable and uniform spherical structure formed by low-molecular weight materials having amphiphilicity, that is, having a hydrophilic group and a hydrophobic group at the same time. When an insoluble drug is dissolved in and introduced to a compound having the micelle structure, the drug is present inside the micelles, and these micelles can have high applicability as a carrier for drug delivery since these micelles can perform target-oriented drug release in the body responding to changes in temperature and pH.

Korean Patent Application No. 10-2001-0035265 discloses a preparation of micelles using a polyethylene glycol and a biodegradable polymer. These materials have advantages in that they all have bioaffinity due to their biodegradability, however, they have disadvantages in that drug delivery in a target area is difficult since these materials are not sensitive to changes in the body, for example, specific changes such as pH changes.

In addition, Korean Patent Application No. 10-2010-0112491 discloses a preparation of micelles using a block copolymer of a poly(β-aminoester) compound and a polyethylene glycol-based compound. These materials have advantages in that they are sensitive to specific changes such as pH changes, however, they have disadvantages in that the control of degradation rate is impossible since degradation occurs due to hydrolysis after dimicellization.

Meanwhile, the pH environment in a body generally indicates pH 7.4 to 7.2, however, it has been known that peripheral pH of abnormal cells such as cancer cells indicates pH 3.0 to 7.0, which is slightly acidic to strongly acidic. Recently, studies have been carried out in which a drug is released at pH 7.0 or lower in order to specifically deliver the drug to cancer cells.

U.S. Pat. No. 5,955,509 having the tile of "pH dependent polymer micelles" discloses a method for preparing pH-sensitive polymer micelles in which a block copolymer of poly (vinyl N-heterocycle) and poly(alkylene oxide) forms micelles at pH 6.0 or higher, and the block copolymer is collapsed between pH 2 and 6, and Japanese Patent Application Laid-Open Publication No. 2002-179556 having the tile of "block copolymer-anti-cancer drug complex medicine" discloses a block copolymer of a hydrophilic polyethylene glycol-based compound and a hydrophobic polyamino acid-based compound forming micelles at a specific pH.

In view of the above, the inventors identified that, when a pH-sensitive block copolymer formed from a polyethylene glycol-based compound and a polyglutamic acid-based compound including a tertiary amine group is used, micelles are collapsed and thereby drugs can be released when pH is 7.0 or less, and micelles are formed and collapsed by the pH difference of 0.2, therefore, the pH-sensitive block copolymer has both pH sensitivity and biodegradability due to peptidase, and thereby control of the degradation rate relating to drug release cycle is possible and the biotoxicity of the residues after degradation can be reduced, thereby completing the present disclosure.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a peptide based block copolymer represented by the following Chemical Formula 1:

[Chemical Formula 1]

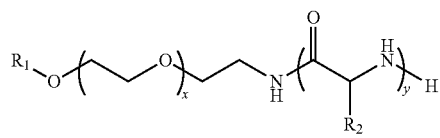

wherein, X is an integer of 10 to 200; Y is an integer of 50 to 100; $R_1$ is hydrogen or $C_{1-4}$ alkyl; $R_2$s are each independently i)

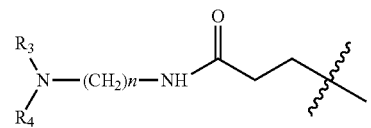

(substituent A) or

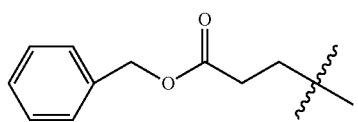 [SMILES: *CCC(=O)OCc1ccccc1]

(substituent B), or ii)

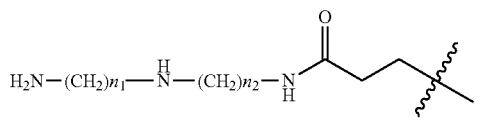

(substituent C) or

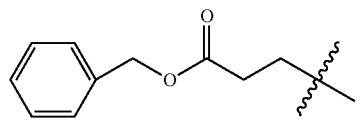 [SMILES: *CCC(=O)OCc1ccccc1]

(substituent B), wherein, 80% or more of y number of $R_2$s are i) the substituent A, or ii) the substituent C; and the above $R_3$ and $R_4$ are $C_{1-6}$ alkyl, the n is an integer of 1 to 6, and the $n_1$ and $n_2$ are each independently integers of 1 to 6.

A process for the preparation thereof, and polymer micelles using the same are also provided.

Other features and aspects will be apparent from the following detailed description, the drawings, and the claims.

BRIEF DESCRIPTION OF THE DRAWINGS

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

Figure 1:
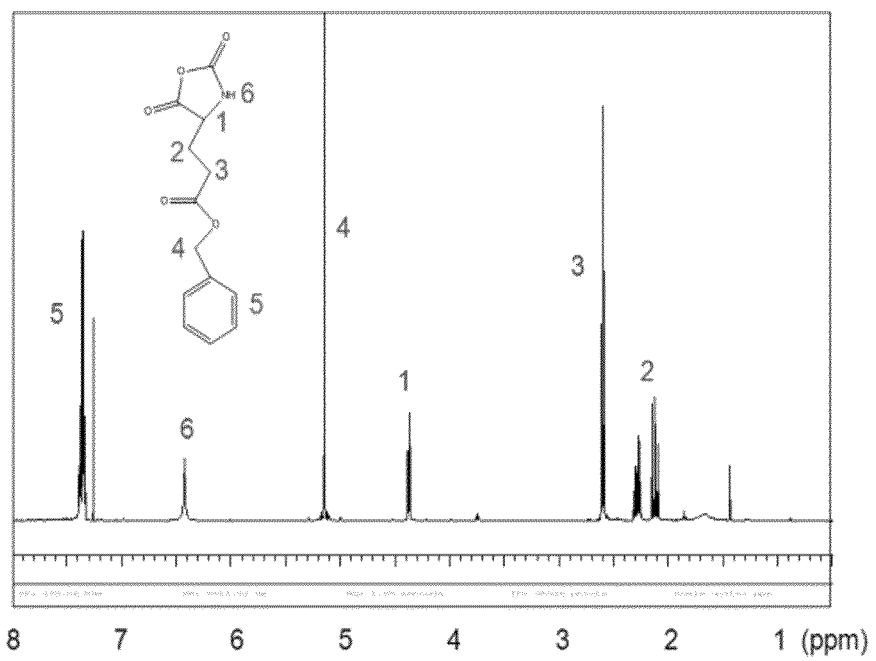
FIG. 1 shows an NMR of benzyl-L-glutamic acid-N-carboxy anhydride (BLG-NCA) prepared in Preparation Example 1.

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

An object of the present disclosure is to provide a polypeptide based block copolymer having biodegradability due to peptidase, and a process for the preparation thereof, and a polymer micelle-type diagnostic and therapeutic composition including the block copolymer.

In order to achieve the above object, the present disclosure provides a peptide based block copolymer represented by the following Chemical Formula 1.

[Chemical Formula 1]

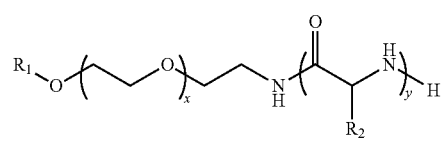

In the formula,

X is an integer of 10 to 200,

Y is an integer of 50 to 100, $R_1$ is hydrogen or $C_{1-4}$ alkyl, $R_2$s are each independently i)

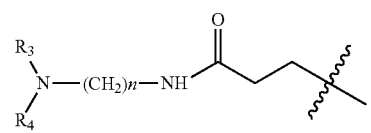

(substituent A) or

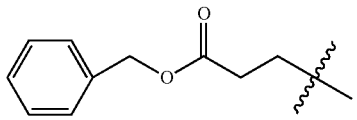

(substituent B), or ii)

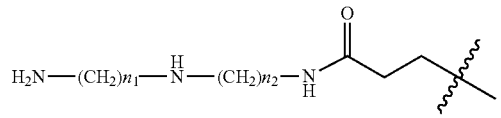

(substituent C) or

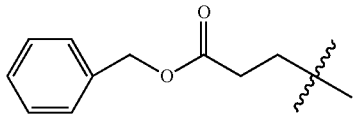 [SMILES: *CCC(=O)OCc1ccccc1]

(substituent B), and herein, 80% or more of y number of $R_2$s are i) the substituent A, or ii) the substituent C, the $R_3$ and $R_4$ are $C_{1-6}$ alkyl, the n is an integer of 1 to 6, and the $n_1$ and $n_2$ are each independently integers of 1 to 6.

In addition, the present disclosure provides a polymer micelle-type drug composition that includes (a) the block copolymer; and (b) a molecular imaging marker for disease diagnosis, a contrast medium, or a therapeutic material including a bioactive substance for disease treatment, which can be included inside the block copolymer.

In addition, the present disclosure provides a method for preparing a block copolymer, which includes the steps of preparing a compound of the following Chemical Formula 2 by reacting glutamic acid, benzyl ester and triphosgene (Step 1); preparing a compound of the following Chemical Formula 4 by copolymerizing the compound of the following Chemical Formula 2 with a compound of the following Chemical Formula 3 (Step 2); and reacting the compound of the following Chemical Formula 4 with a compound of the following Chemical Formula 5 or a compound of the following Chemical Formula 6 (Step 3).

[Chemical Formula 2]

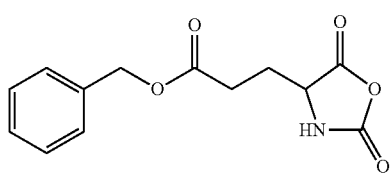

[Chemical Formula 3]

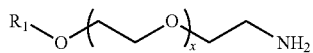

[Chemical Formula 4]

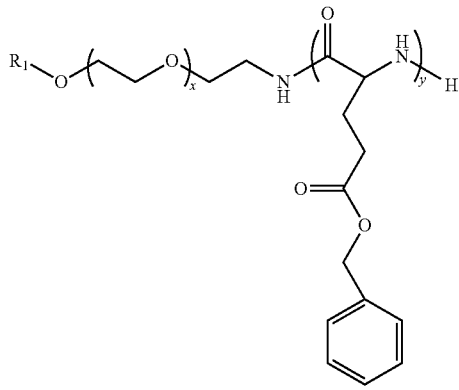

[Chemical Formula 5]

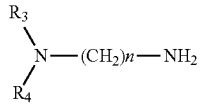

[Chemical Formula 6]

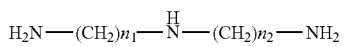

In the formulae, x, y, $R_1$, $R_3$, $R_4$, n, $n_1$ and $n_2$ are the same as those defined above.

Hereinafter, the present disclosure will be described in detail.

The polyglutamic acid-based compound block of the block copolymer of the present disclosure includes a tertiary amine group (—N=) that is ionized at pH 7.0 or lower, and includes a glutamic acid group that is dimicellized and degraded due to peptidase when the pH ranges from 6.5 to 7.0. In addition, the polyglutamic acid-based compound block of the block copolymer of the present disclosure includes

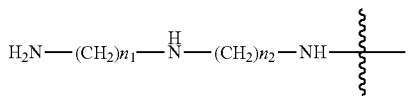

that is ionized at pH 7.0 or lower, and includes a glutamic acid group that is dimicellized and degraded due to peptidase when the pH ranges from 6.5 to 7.0.

$R_2$s of the Chemical Formula 1 of the present disclosure are each independently

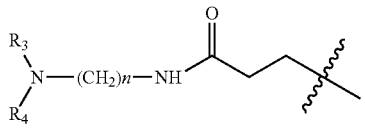

(substituent A) or

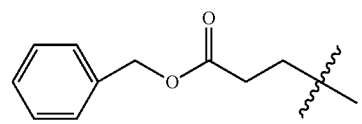 [SMILES: *CCC(=O)OCc1ccccc1]

(substituent B), and herein, 80% or more of y number of $R_2$s are the above substituent A.

In addition, in the present disclosure, it is preferable that 88% or more of y number of $R_2$s of the Chemical Formula 1 be the substituent A. Furthermore, in the present disclosure, it is more preferable that 93% or more of y number of $R_2$s of the Chemical Formula 1 be the above substituent A. In addition, in the present disclosure, it is even more preferable that 96% or more of y number of $R_2$s of the Chemical Formula 1 be the above substituent A.

Furthermore, $R_2$s of the Chemical Formula 1 of the present disclosure are each independently

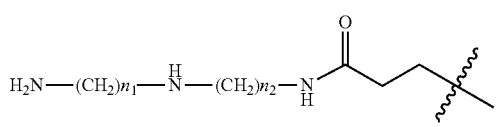

(substituent C) or

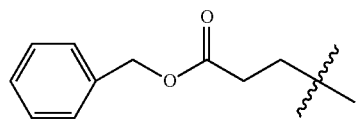 [SMILES: *CCC(=O)OCc1ccccc1]

(substituent B), and herein, 80% or more of y number of $R_2$s are the substituent C.

The block copolymer of the present disclosure includes a tertiary amine group that is ionized at pH 7.0 or lower, and a glutamic acid group that is degraded due to peptidase, therefore, the block copolymer is sensitive to pH changes in the body, forms a micelle structure at a specific pH range, is dimicellized and degraded due to peptidase when the pH ranges from 6.5 to 7.0 and thereby control of degradation rate is possible.

Traditional poly(β-aminoester) compounds have an ester group in the main chain and the chain is degraded due to hydrolysis, therefore, degradation products having a carboxylic acid group (—COOH) at the end are produced when the compound is degraded in the body. As a result, these degradation products, which have low acidity, can cause fatal damage to the tissues in the body. In contrast, in the present disclosure, a polymer is formed based on a polypeptide and degradation occurs due to polypeptidase in the body, therefore the polymer has bioaffinity since degradation products that have low acidity are not produced.

In addition, when the polymer based on a polypeptide of the present disclosure is formed and the glutamic acid is used as a base, a block copolymer of the Chemical Formula 1 can be prepared by an aminolysis reaction between benzyl glutamic acid and tertiary amine in which the end of one alkyl group is effectively substituted with $NH_2$, and by controlling the reaction time of the aminolysis reaction, the ratio of

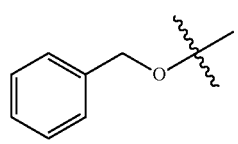

being converted to

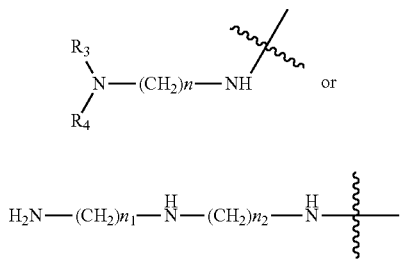

can be controlled. Furthermore, when the conversion ratio is 80% or more, pH-dependent properties are distinctively shown.

In addition, when a polyglutamic acid-based compound that includes a traditional tertiary amine group is used alone, pH-dependence is shown, however, micelles due to a self-assembly phenomenon cannot be formed. However, in the present disclosure, micelles due to a self-assembly phenomenon can be formed by forming a block copolymer of a polyglutamic acid-based compound including a tertiary amine group and a hydrophilic polyethylene glycol-based compound. Therefore, the block copolymer prepared according to the present disclosure can be used as a carrier for target-oriented drug release as a diagnostic and therapeutic agent for disease by forming a micelle structure capable of target release at a specific pH.

In addition, traditional drug delivery agents have problems in that the drug accumulates in the body as a residue after the drug is delivered to a target area causing various side effects, and biodegradable polymers designed to avoid this problem also have problems in that the control of degradation rate is difficult since biodegradation occurs due to hydrolysis. Therefore, the copolymer is prepared using protein constituents such as glutamic acid as the monomer of the block copolymer, and there are advantages in that the dimicellized copolymer is biodegraded due to peptidase in the body and can be completely eliminated from the body, and the degradation rate can be controlled.

The average molecular weight (Mn) of the copolymer of the present disclosure is not particularly limited, however, in the Chemical Formula 1, it is preferable that x be an integer ranging from 10 to 200, and y be an integer ranging from 50 to 100. In addition, it is more preferable that the x be an integer of 10 to 100, and the y be an integer of 50 to 100. If the value of the x is less than 10 and greater than 200, the control of the molecular weight of the final block copolymer is not only difficult, but the formation of micelles using the block copolymer is not simple. In addition, if the value of the y is less than 10, it is difficult to form block copolymer micelles at a specific pH, and even if the micelles are formed, they tend to be dissolved in water and collapsed. When the value of the y is greater than 200, the block copolymer may be precipitated without forming micelles at a specific pH since hydrophilicity/hydrophobicity balance is broken.

In the Chemical Formula 1 of the present disclosure, $R_1$ is preferably methyl. In addition, in the Chemical Formula 1 of the present disclosure, $R_3$ and $R_4$ are preferably isopropyl or n-butyl. Also, in the Chemical Formula 1 of the present disclosure, n of

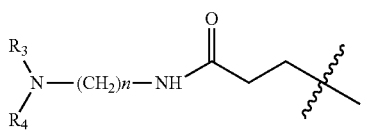

is preferably 2. In addition, in the Chemical Formula 1 of the present disclosure, m and $n_2$ of

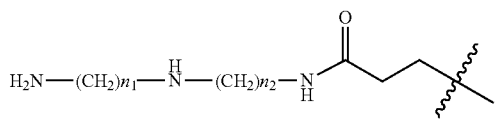

are preferably 2.

In the pH-sensitive micelles of the present disclosure, stable micelles are formed at a specific pH, for example, in the range of pH 7.2 to 7.8, which is the pH range of normal cells in the body, and the micelle structure is collapsed in the range of pH 6.5 to 7.0, which is the pH range in which abnormal cells such as cancer cells are present. Therefore, the micelles can be used as a carrier for target-oriented drug release, which can either diagnose targeting the cancer cells by releasing the diagnostic agent included inside the micelles or treat the cancer cells by releasing the therapeutic agent included inside the micelles. In other words, micelles cannot be formed at a low pH (pH 7.0 or lower) since the whole block copolymer becomes soluble due to the increase of ionization of the tertiary amine present in the polyglutamic acid-based compound including the tertiary amine group, and in the range of pH 7.2 to 7.8, micelles due to self-assembly are formed since hydrophobicity is shown due to the decrease of ionization of the tertiary amine The block copolymer of the present disclosure can be used in the field of gene transfer and drug delivery, and can also be applied to the use in which diagnosis and treatment are performed simultaneously by delivering the substances for disease diagnosis and treatment to the abnormal cells.

In addition, in the present disclosure, target-oriented micelles targeting cancer cells are designed and applied in which micelles are formed in the range of pH 7.2 to 7.8, the same condition as that of normal body, and micelles are collapsed at pH 7 or lower, an abnormal condition such as the presence of cancer cells. However, by appropriately changing the constituents of the block copolymer, the molar ratio thereof, molecular weight and/or functional groups within the block, target-oriented micelles targeting gene mutation or other application fields besides cancer cells can be designed and applied.

As one of the constituents of the block copolymer that forms pH-sensitive micelles according to the present disclosure, common biodegradable compounds having hydrophilicity known in the related art, for example, polyethylene glycol-based compounds, may be used. In particular, the polyethylene glycol-based compound preferably has a monofunctional group such as an amine group at the end so as to react with a polyglutamic acid-based compound, and one example includes a compound of the following Chemical Formula 3 in which the end of the molecule is substituted with $NH_2$.

[Chemical Formula 3]

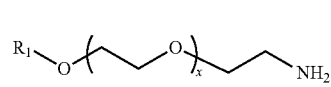

In the formula, x is an integer of 10 to 200, and
$R_1$ is hydrogen or $C_1$ alkyl.

A method for preparing the pH-sensitive block copolymer according to the present disclosure includes the step of preparing a compound of the following Chemical Formula 2 by reacting glutamic acid, benzyl ester and triphosgene (Step 1); the step of preparing a compound of the following Chemical Formula 4 by copolymerizing the compound of the following Chemical Formula 2 with a compound of the following Chemical Formula 3 (Step 2); and the step of reacting the compound of the following Chemical Formula 4 with a compound of the following Chemical Formula 5 or a compound of the following Chemical Formula 6 (Step 3).

[Chemical Formula 2]

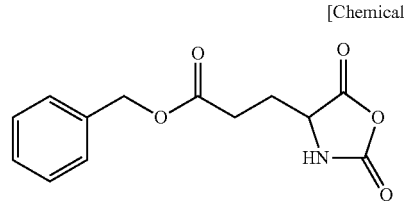

[Chemical Formula 3]

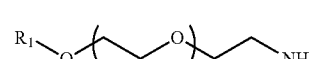

[Chemical Formula 4]

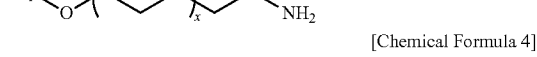

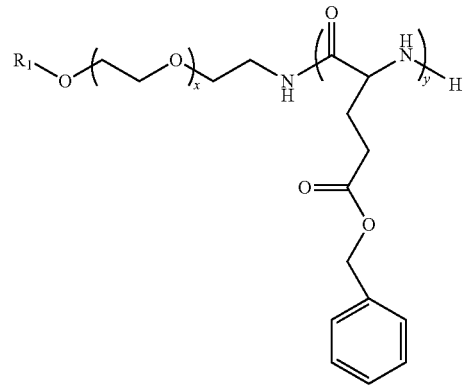

[Chemical Formula 5]

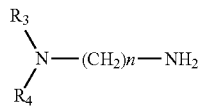

[Chemical Formula 6]

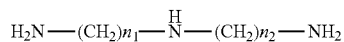

Each step of the preparation method will be described using one example. In the Step 1, in which the compound of the Chemical Formula 2 is prepared by reacting glutamic acid, benzyl ester and triphosgene, glutamic acid, benzyl ester and triphosgene are reacted first in the presence of an anhydrous tetrahydrofuran solvent, and it is preferable that the reaction be carried out under nitrogen atmosphere at 50° C. After the reaction has completed, the solution is introduced to hexane, recrystallized using 1:1 hexane/ethyl acetate as a recrystallization solvent, and the compound of the Chemical Formula 2 can be obtained.

In the Step 2, in which the compound of the Chemical Formula 4 (PEG-b-PBLG) is prepared by copolymerizing the compound of the Chemical Formula 2 with the compound of the Chemical Formula 3, the compound of the Chemical Formula 3 and benzyl-L-glutamic acid-N-carboxy anhydride (BLG-NCA) of the Chemical Formula 2 prepared in the Step 1 are reacted first by being dissolved in anhydrous chloroform in various molar ratios. Preferably, the compound of the Chemical Formula 2 (BLG-NCA) and the compound of the Chemical Formula 3 (PEG-NH2) are copolymerized in a molar ratio ranging from 10 to 1 to 50 to 1. It is preferable that the above reaction be carried out under nitrogen atmosphere for 72 hours at room temperature. After the reaction has completed, a copolymer of a polyglutamic acid-based compound block and a polyethylene glycol-based block, which has a molecular weight of Mn=10,000 to 20,000, is formed.

In the step of reacting the compound of the Chemical Formula 4 with the compound of the Chemical Formula 5, part of y number of

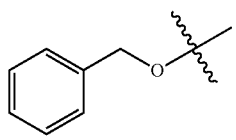 [SMILES: *OCc1ccccc1]

of the Chemical Formula 4 are converted to

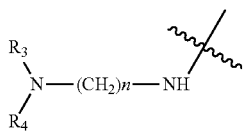

by controlling the time of reacting the compound of the Chemical Formula 4 with the tertiary amine in which the end of one alkyl group of the Chemical Formula 5 is substituted with $NH_2$.

In addition, in the step of reacting the compound of the Chemical Formula 4 with the compound of the Chemical Formula 6, part of y number of

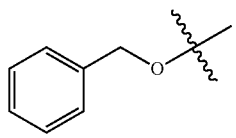

of the Chemical Formula 4 are converted to

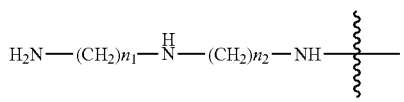

by controlling the time of reacting the compound of the Chemical Formula 4 with the triamine of the Chemical Formula 6.

In this case, the compound of the Chemical Formula 4 prepared in the Step 2 is dissolved in anhydrous N,N-dimethylformamide, and is reacted with the compound of the Chemical Formula 5 or the compound of the Chemical Formula 6. It is preferable that the reaction be carried out in an oil bath at 55° C. In addition, it is preferable that the reaction be carried out adding 2-hydroxypyridine (2-HP).

Furthermore, the reaction time in the Step 3 is preferably 36 hours to 72 hours. By controlling the reaction time to be 36 hours to 72 hours, 80% or more of y number of

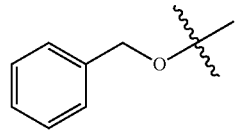 [SMILES: *OCc1ccccc1]

can be converted to

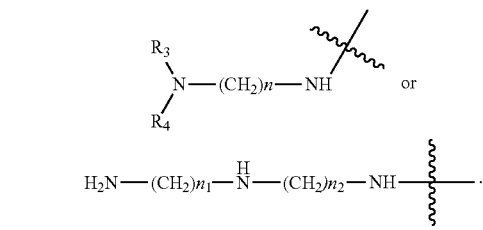

In other words, an amine group is introduced depending on the reaction time of the aminolysis reaction by converting

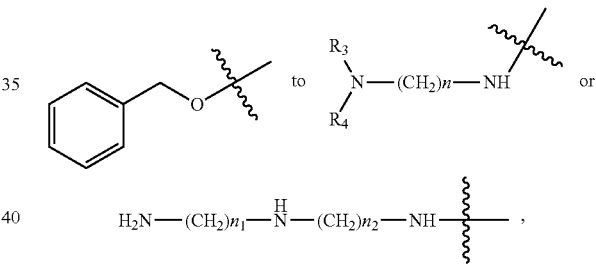

therefore, the conversion ratio increases as the reaction time increases. According to one example of the present disclosure, if the reaction time is less than 36 hours, the conversion ratio is less than 80%, and the copolymer is not completely soluble in an aqueous solution and does not have pH-sensitivity.

In the present disclosure, $^1$H-NMR is used to measure the molecular weight of the block copolymer synthesized as above, and fluorescence spectrometer (FL) and dynamic light scattering (DLS) are used to measure the changes in the micelle concentration depending on the changes in pH and the changes in micelle sizes, and the applicability as pH-sensitive micelles was able to be verified through the analyses described above.

In a polymer micelle-type drug composition of the present disclosure, which includes (a) the block copolymer; and (b) a molecular imaging marker for disease diagnosis, a contrast medium, or a therapeutic material for disease treatment, which can be included inside the block copolymer, micelles are formed when the polymer micelle-type drug composition is injected into the body, and the micelles are collapsed when the polymer micelle-type drug composition reached to a region having topically low pH such as cancer cells, and as a result, target-oriented drug delivery can be performed through the release of the molecular imaging marker for disease diagnosis, the contrast medium, or the therapeutic material for disease treatment, which are included inside.

The molecular imaging marker, the contrast medium and the therapeutic material that can be included in the polymer micelle-type block copolymer of the present disclosure can be used without particular limitation Unlimited examples thereof include pyrene, RITC, FTC, ICG (Indocyanine Green), iron oxide, manganese oxide, or the like, as the molecular imaging marker, and anticancer drugs, antimicrobial agents, steroids, anti-inflammatory analgestic drugs, sex hormone drugs, immunosuppressive drugs, antiviral agents, anesthetic drugs, antiemetic drugs, antihistamines, or the like, as the therapeutic drug. In addition, typical additives known in the related art such as diluting agents, stabilizers, pH control agents, antioxidants, preserved agents, binding agents, disintegrating agents, or the like, may be included in addition to the ingredients described above.

As the method for preparing the polymer micelles according to the present disclosure, methods such as stirring, heating, ultrasonic scan, a solvent evaporation method using an emulsification method, matrix formation, a dialysis method using an organic solvent can be used either alone or in combination.

The diameter of the prepared polymer micelles is not particularly limited, however, the range of 10 to 200 nm is preferable. In addition, the polymer micelle drug composition can be used as a pharmaceutical preparation in the form of oral agents or non-oral agents, and may be prepared as intravenous injections, intramuscular injections or hypodermic injections.

The block copolymer according to the present disclosure has advantages in that a degradation rate is controlled since the block copolymer not only has pH sensitivity but has biodegradability due to peptidase in the body. In addition, the block copolymer has bioaffinity since the occurrence of degradation products having a carboxylic acid group (—COOH) at the end due to the chain degradation by hydrolysis can be prevented. Furthermore, the block copolymer can be changed variously by varying the amine compound used in the block copolymer preparation. Therefore, the block copolymer according to the present disclosure is effective in that the block copolymer can be used as a target-oriented drug delivery agent depending on the pH changes in the body, and as a drug delivery agent having bioaffinity, which can control the rate of degradation.

EXAMPLES

Hereinafter, the present disclosure will be described in more detail with reference to examples. However, these examples are for illustrative purposes only and the scope of the present disclosure is not limited to these examples.

Preparation Example 1

Preparation of poly(ethylene glycol)-block-poly(benzyl-L-glutamic Acid) Copolymer 10 g of L-glutamic acid-benzyl ester and 6.255 g of triphosgene were mixed with 100 mL of anhydrous tetrahydrofuran. The reaction was carried out under nitrogen atmosphere at 50° C. After 2 hours and the reaction has completed, the above solution was introduced to hexane, and the mixture was recrystallized twice using 1:1 hexane/ethyl acetate as a recrystallization solvent, resulting in benzyl-L-glutamic acid-N-carboxy anhydride (BLG-NCA). The yield was 73%. The $^1$H NMR (500 MHz, CDCl$_3$) measurement result of the BLG-NCA obtained above is shown in FIG. 1.

The benzyl-L-glutamic acid-N-carboxy anhydride (BLG-NCA) prepared above and polyethylene glycol of

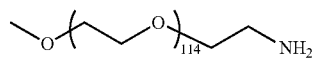

were dissolved in anhydrous chloroform in a molar ratio of 20 to 1. The reaction was carried out under nitrogen atmosphere for 72 hours at room temperature. After the reaction has completed, poly(ethylene glycol)-block-poly(benzyl-L-glutamic acid) (PEG-b-PBLG), a copolymer of a polyglutamic acid block and a polyethylene glycol block, which has a molecular weight of Mn=11,570, was formed. The reactant that has not been reacted was precipitated using a mixture of excess ethanol/ethyl ether, and then filtered.

Preparation Example 2

Preparation of poly(ethylene glycol)-block-poly(benzyl-L-glutamic Acid) Copolymer The benzyl-L-glutamic acid-N-carboxy anhydride (BLG-NCA) prepared in the same manner as in Example 1 and polyethylene glycol of

Figure 2:
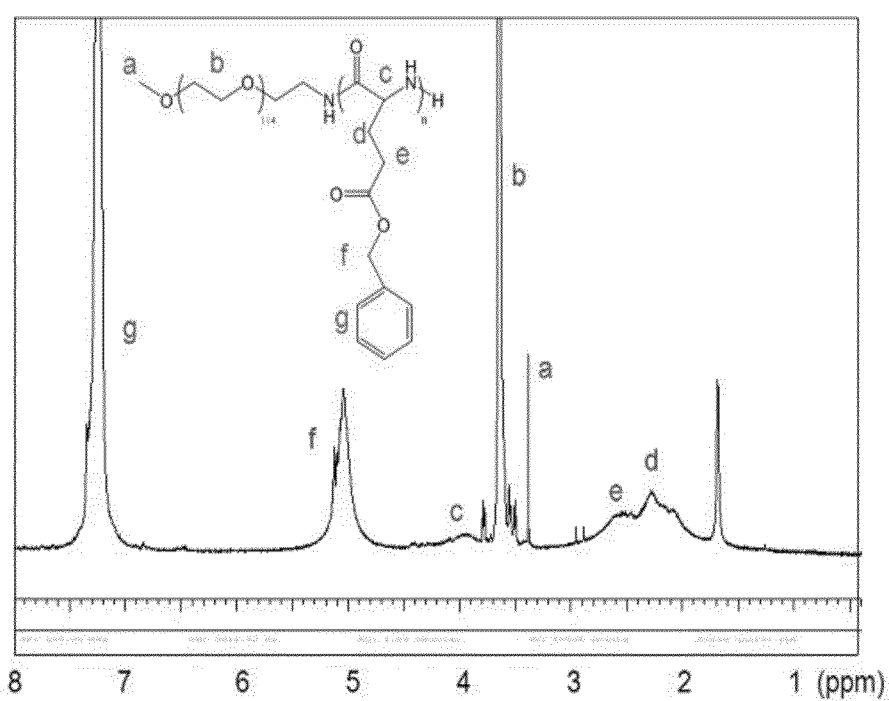
FIG. 2 shows an NMR of poly(ethylene glycol)-block-poly (benzyl-L-glutamic acid) (PEG-b-PBLG) prepared in Preparation Example 2.

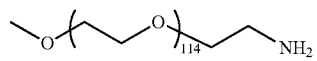

was dissolved in anhydrous chloroform in a molar ratio of 30 to 1. The reaction was carried out under nitrogen atmosphere for 72 hours at room temperature. After the reaction has completed, poly(ethylene glycol)-block-poly(benzyl-L-glutamic acid) (PEG-b-PBLG), a copolymer of a polyglutamic acid block and a polyethylene glycol block, which has a molecular weight of Mn=13,541, was formed. The reactant that has not been reacted was precipitated using a mixture of excess ethanol/ethyl ether, and then filtered. The $^1$H NMR (500 MHz, CDCl$_3$) measurement result of the copolymer obtained above is shown in FIG. 2.

Preparation Example 3

Preparation of poly(ethylene glycol)-block-poly(benzyl-L-glutamic Acid) Copolymer The benzyl-L-glutamic acid-N-carboxy anhydride (BLG-NCA) prepared in the same manner as in Example 1 and polyethylene glycol of

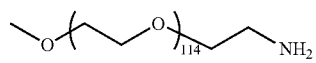

was dissolved in anhydrous chloroform in a molar ratio of 40 to 1. The reaction was carried out under nitrogen atmosphere for 72 hours at room temperature. After the reaction has completed, poly(ethylene glycol)-block-poly(benzyl-L-glutamic acid) (PEG-b-PBLG), a copolymer of a polyglutamic acid block and a polyethylene glycol block, which has a molecular weight of Mn=17,045, was formed. The reactant that has not been reacted was precipitated using a mixture of excess ethanol/ethyl ether, and then filtered.

Example 1

Preparation of poly(ethylene glycol)-block-poly(2-(dibutylamino)-ethyl-L-glutamic Acid Block Copolymer (PEG-b-PN4LG)

Poly(ethylene glycol)-block-poly(benzyl-L-glutamic acid) (PEG-b-PBLG) (10 g) prepared in the above Preparation Example 2 was dissolved in anhydrous N,N-dimethylformamide (10 mL/1 g). Then, the mixture was introduced in an oil bath, and the temperature was raised to 55° C. After that, 2-(dibutylamino)ethylamine (100 g) and 2-hydroxypyridine (13.82 g) were added. The reaction was carried out for 36 hours, and a final product, poly(ethylene glycol)-block-poly(2-(dibutylamino)ethyl-L-glutamic acid) (PEG-b-PN4LG) in which 80% of the benzyl group was converted to the dibutylamino group, was obtained after being precipitated using ether and then filtered. The final product was dried under vacuum condition for 48 hours. A block copolymer in which the number average molecular weight of the whole block copolymer was 12,823, was obtained, and the yield was 70% or more.

Example 2

Preparation of poly(ethylene glycol)-block-poly(2-(dibutylamino)-ethyl-L-glutamic Acid Block Copolymer (PEG-b-PN4LG)

A block copolymer in which the number average molecular weight of the whole block copolymer was 13,942 and the conversion ratio was 88% was obtained by the same reaction as in Example 1 except that the reaction time of 2-(dibutylamino)ethylamine and 2-hydroxypyridine addition was 48 hours. The yield of the final product was 70% or more.

Example 3

Preparation of poly(ethylene glycol)-block-poly(2-(dibutylamino)-ethyl-L-glutamic Acid Block Copolymer (PEG-b-PN4LG)

A block copolymer in which the number average molecular weight of the whole block copolymer was 12,340 and the conversion ratio was 93% was obtained by the same reaction as in Example 1 except that the reaction time of 2-(dibutylamino)ethylamine and 2-hydroxypyridine addition was 60 hours. The yield of the final product was 70% or more.

Example 4

Preparation of poly(ethylene glycol)-block-poly(2-(dibutylamino)-ethyl-L-glutamic Acid Block Copolymer (PEG-b-PN4LG)

Figure 3:
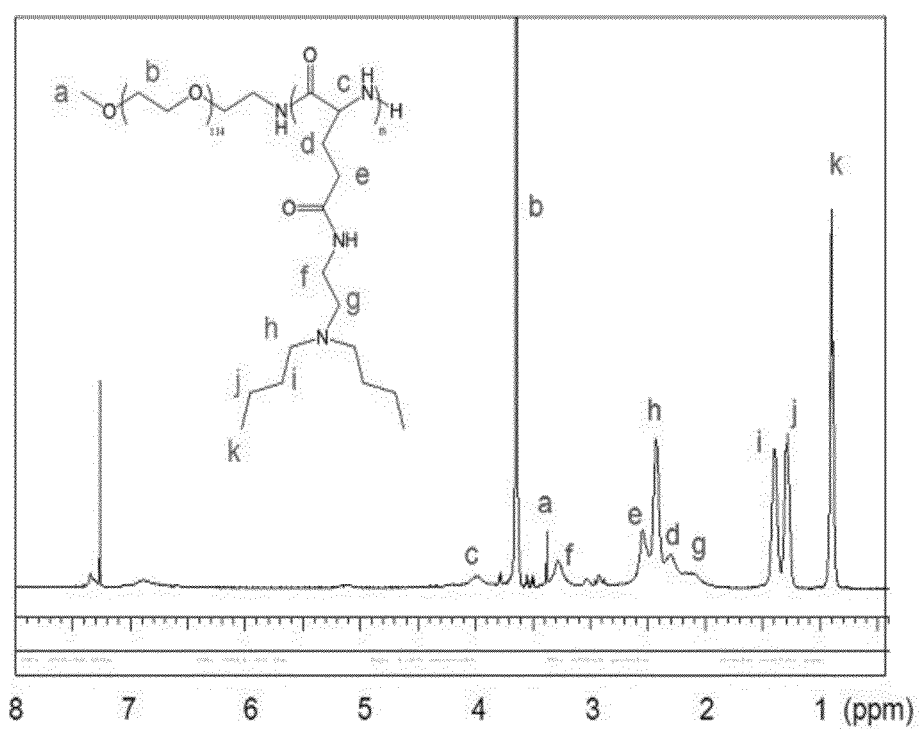
FIG. 3 shows an NMR of poly(ethylene glycol)-block-poly (2-(dibutylamino)ethyl-L-glutamic acid) (PEG-b-PN4LG) prepared in Example 4.

A block copolymer in which the number average molecular weight of the whole block copolymer was 12,011 and the conversion ratio was 96% was obtained by the same reaction as in Example 1 except that the reaction time of 2-(dibutylamino)ethylamine and 2-hydroxypyridine addition was 72 hours. The yield of the final product was 70% or more. The $^1$H NMR (500 MHz, CDCl$_3$) measurement result of the copolymer obtained above is shown in FIG. 3.

Example 5

Preparation of poly(ethylene glycol)-block-poly(2-(diisopropylamino)-ethyl-L-glutamic Acid Block Copolymer (PEG-b-PN3LG)

Poly(ethylene glycol)-block-poly(benzyl-L-glutamic acid) (PEG-b-PBLG) (10 g) prepared in the above Preparation Example 2 was dissolved in anhydrous N,N-dimethylformamide (10 mL/1 g). Then, the mixture was introduced in an oil bath, and the temperature was raised to 55° C. After that, 2-(diisopropylamino)ethylamine (80 g) and 2-hydroxypyridine (13.82 g) were added. The reaction was carried out for 72 hours, and a final product, poly(ethylene glycol)-block-poly(2-(diisopropylamino)ethyl-L-glutamic acid) (PEG-b-PN3LG) in which 95% of the benzyl group was converted to the diisopropylamino group, was obtained after being precipitated using ether and then filtered. The final product was dried under vacuum condition for 48 hours. A block copolymer in which the number average molecular weight of the whole block copolymer was 12,959, was obtained, and the yield was 70% or more.

Example 6

Preparation of poly(ethylene glycol)-block-poly[(2-aminoethyl)-2-aminoethyl]-L-glutamic Acid Block Copolymer (PEG-b-PNLG)

Poly(ethylene glycol)-block-poly(benzyl-L-glutamic acid) (PEG-b-PBLG) (10 g) prepared in the above Preparation Example 2 was dissolved in anhydrous N,N-dimethylformamide (10 mL/1 g). Then, the mixture was introduced in an oil bath, and the temperature was raised to 55° C. After that, diethylenetriamine (60 g) and 2-hydroxypyridine (13.82 g) were added. The reaction was carried out for 72 hours, and a final product, poly(ethylene glycol)-block-poly[(2-aminoethyl)-2-aminoethyl]-L-glutamic acid) (PEG-b-PN3LG) in which 95% of the benzyl group was converted to the ethylamino group, was obtained after being precipitated using ether and then filtered. The final product was dried under vacuum condition for 48 hours. A block copolymer in which the number average molecular weight of the whole block copolymer was 14,000, was obtained, and the yield was 70% or more.

Comparative Example 1

Preparation of poly(ethylene glycol)-block-poly(2-(dibutylamino)-ethyl-L-glutamic Acid Block Copolymer (PEG-b-PN4LG)

A block copolymer in which the number average molecular weight of the whole block copolymer was 11,115 and the conversion ratio was 40% was obtained by the same reaction as in Example 1 except that the reaction time of 2-(dibutylamino)ethylamine and 2-hydroxypyridine addition was 12 hours. The yield of the final product was 70% or more.

Comparative Example 2

Preparation of poly(ethylene glycol)-block-poly(2-(dibutylamino)-ethyl-L-glutamic Acid Block Copolymer (PEG-b-PN4LG)

A block copolymer in which the number average molecular weight of the whole block copolymer was 11,216 and the conversion ratio was 63% was obtained by the same reaction as in Example 1 except that the reaction time of 2-(dibutylamino)ethylamine and 2-hydroxypyridine addition was 24 hours. The yield of the final product was 70% or more.

Test Example 1

Evaluation of Conversion Ratio by Reaction Time

Figure 4:
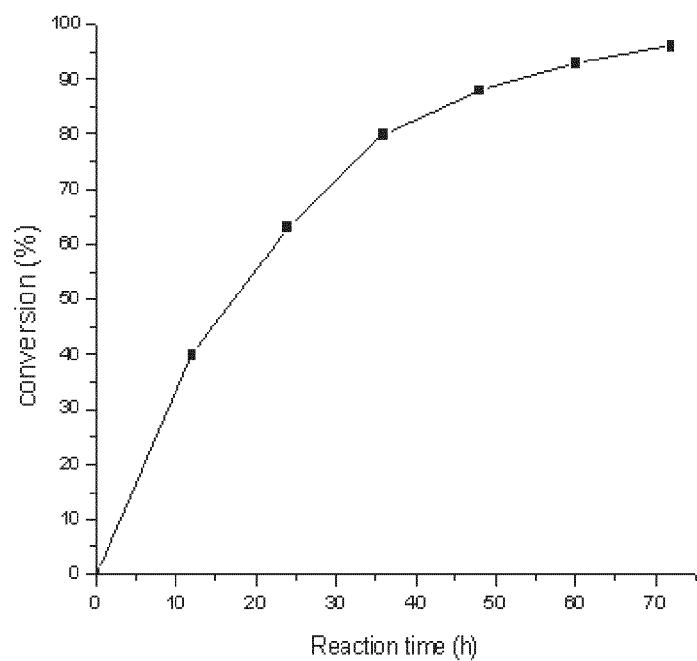
FIG. 4 is a graph that shows the ratio of the benzyl group of poly(ethylene glycol)-block-poly(benzyl-L-glutamic acid) (PEG-b-PBLG) described in the above Examples 1 to 4 and Comparative Examples 1 and 2 being converted to a (dibutylamino)ethylamine group as the reaction time progresses.

The poly(ethylene glycol)-block-poly(2-(dibutylamino)-ethyl-L-glutamic acid) copolymer (PEG-b-PNLG) prepared in Examples 1 to 6 was sampled by the reaction time, and the conversion ratio was evaluated using $^1$H-NMR (FIG. 4). In other words, the conversion ratio was evaluated using $^1$H-NMR by measuring the increase of a specific peak area of PNLG having a tertiary amine group. As shown in the following Table 1, it was identified that the ratio of conversion to the tertiary amine group increased as the reaction time increased.

TABLE 1

| | Polymer Type | Reaction Time | Conversion Ratio |
|---|---|---|---|
| Preparation Example 1 | PEG-b-PBLG | 72 h | — |
| Preparation Example 2 | PEG-b-PBLG | 72 h | — |
| Preparation Example 3 | PEG-b-PBLG | 72 h | — |
| Comparative Example 1 | PEG-b-PN4LG | 12 h | 40% |
| Comparative Example 2 | PEG-b-PN4LG | 22 h | 63% |
| Example 1 | PEG-b-PN4LG | 36 h | 80% |
| Example 2 | PEG-b-PN4LG | 48 h | 88% |
| Example 3 | PEG-b-PN4LG | 60 h | 93% |
| Example 4 | PEG-b-PN4LG | 72 h | 96% |
| Example 5 | PEG-b-PN3LG | 72 h | 95% |
| Example 6 | PEG-b-PNLG | 72 h | 95% |

Test Example 2

Measurement of Changes in Micelles Due to Changes in pH

Test Example 2-1

Measurement of pKb Value of pH-Sensitive Copolymer

Figure 5:
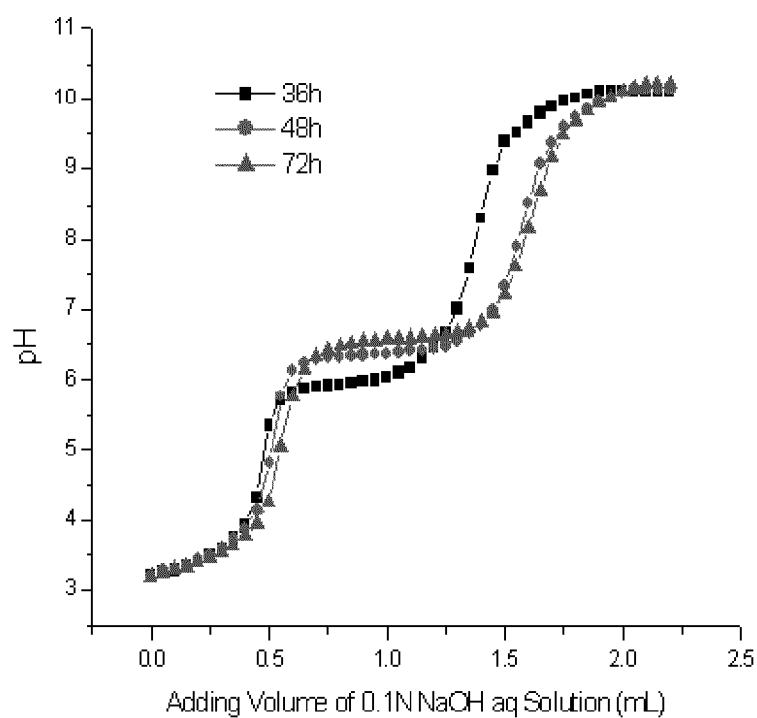
FIG. 5 is a graph that shows a pKb value determined by titrimetry using a NaOH aqueous solution of a polypeptide based block copolymer.

A pKb value was measured by titrimetry using a NaOH aqueous solution utilizing the block copolymer (PEG-b-PNLG) prepared in the Examples 1 to 5, which has different molecular weights depending on the reaction time (FIG. 5). As shown in FIG. 5, it was verified that the more the reaction time increased, that is, the more the PNLG having a tertiary amine group was produced, the acid-based inflection point was changed rapidly, and the pKb value more or less increased. The measured pKb value is shown in the following Table 3.

Test Example 2-2

Figure 6:
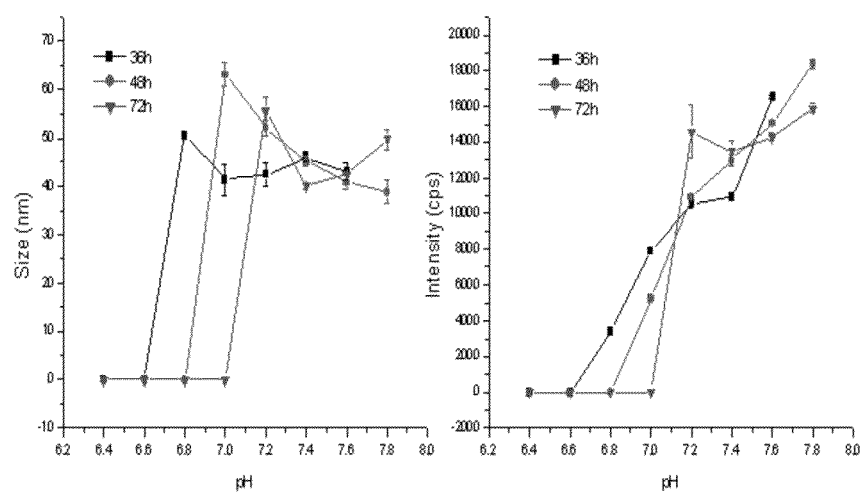
FIG. 6 shows the changes in the sizes of micelles and the changes in the intensity of dynamic light scattering (DIS) due to the pH changes of poly(ethylene glycol)-block-poly(2-(dibutylamino)-ethyl-L-glutamic acid) (PEG-b-PN4LG) prepared in Example 1 (36 h), Example 2 (48 h) and Example 4 (72 h).

Measurement of Changes in Micelle Sizes and Dynamic Light Scattering (DLS) Intensities Due to pH Changes of pH-Sensitive Copolymer The changes in micelle sizes and intensities of poly(ethylene glycol)-block-poly(2-(dibutylamino)-ethyl-L-glutamic acid) (PEG-b-PN4LG) prepared in Examples 1 to 6 were measured at pH 7.8, pH 7.4, pH 7.2, pH 7.0, pH 6.8 and pH 6.6 using a dynamic light scattering method (DLS) (FIG. 6).

As the result of the test, it was seen that micelles having certain sizes are present at pH 7.0 or higher, however, it was identified that, at a pH of lower than 7.0, PN4LG was completely ionized and micelles were not formed at all.

As a result, it was verified that the block copolymer of the present disclosure, which was formed by the copolymerization of hydrophobic PN4LG and a hydrophilic PEG compound, can form or collapse polymer micelles through a reversible self-assembly phenomenon due to pH changes and the amphiphilicity present within the copolymer.

In addition, it was identified that the copolymers prepared in Preparation Examples 1 to 3 and the copolymers of which reaction time was adjusted to 12 hours to 22 hours were insoluble or not completely soluble in an aqueous solution (Table 2).

TABLE 2

| | Polymer Type | Reaction Time | Solubility in Aqueous Solution |
|---|---|---|---|
| Preparation Example 1 | PEG-b-PBLG | 72 h | Insoluble |
| Preparation Example 2 | PEG-b-PBLG | 72 h | Insoluble |
| Preparation Example 3 | PEG-b-PBLG | 72 h | Insoluble |
| Comparative Example 1 | PEG-b-PN4LG | 12 h | Insoluble |
| Comparative Example 2 | PEG-b-PN4LG | 22 h | Not Completely Soluble |
| Example 1 | PEG-b-PN4LG | 36 h | pH dependent |
| Example 2 | PEG-b-PN4LG | 48 h | pH dependent |
| Example 3 | PEG-b-PN4LG | 60 h | pH dependent |
| Example 4 | PEG-b-PN4LG | 72 h | pH dependent |
| Example 5 | PEG-b-PN3LG | 72 h | pH dependent |
| Example 6 | PEG-b-PNLG | 72 h | pH dependent |

Test Example 2-3

Measurement of Changes in Fluorescence Analysis (FL) of pH-Sensitive Copolymer

Figure 7:
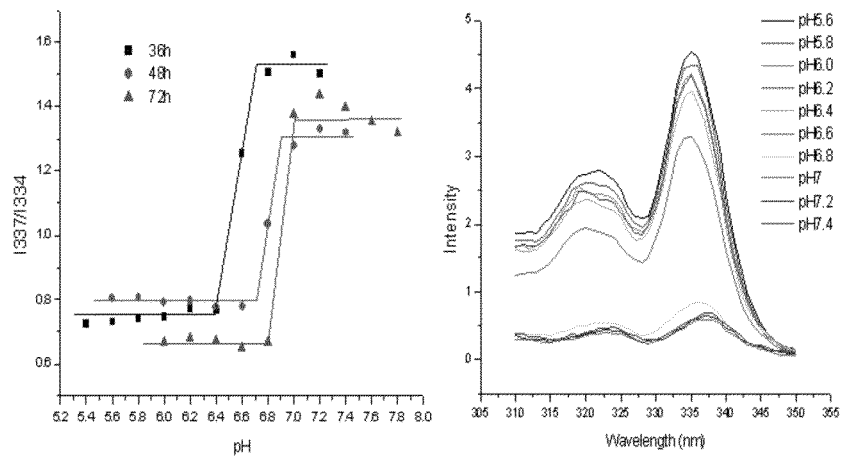
FIG. 7 shows the result of fluorescence analysis (FL) of the micelles due to the pH changes of poly(ethylene glycol)-block-poly(2-(dibutylamino)-ethyl-L-glutamic acid) (PEG-b-PN4LG) prepared in Example 1 (36 h), Example 2 (48 h) and Example 4 (72 h), and the intensity of fluorescence analysis (FL) depending on the wavelength (nm) of poly (ethylene glycol)-block-poly(2-(dibutylamino)-ethyl-L-glutamic acid) (PEG-b-PN4LG) prepared in Example 2 (48 h).

The changes in the fluorescence analysis (FL) of the micelles due to the pH changes of poly(ethylene glycol)-block-poly(2-(dibutylamino)-ethyl-L-glutamic acid) (PEG-b-PNLG) prepared in Example 1, Example 2 and Example 4 were measured (FIG. 7). Pyrene, a hydrophobic light emitting material, was used since the behavioral changes of the micelles cannot be directly determined using a fluorescence spectrometer.

A buffer solution of pH 6 containing $10^{-6}$ M of pyrene was prepared, and the pH of the solution was raised to pH 8.0 after each copolymer prepared in Examples 1 to 6 was dissolved to have the concentration of 1 mg/ml. After that, 5M hydrochloric solution was added dropwise so that the pH was changed to the range of 5.5 to 8.0, and the changes in the emitted energy due to the concentration changes of the micelles were measured using a fluorescence spectrometer.

Test Example 2-4

Measurement of Critical Micelle Concentration (CMC) of pH-Sensitive Copolymer

Figure 8:
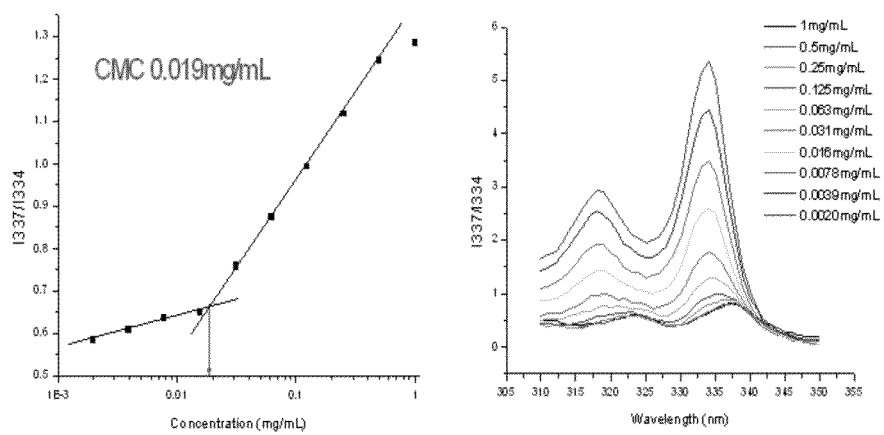
FIG. 8 shows the measurement results of critical micelle concentration (CMC) of poly(ethylene glycol)-block-poly(2-(dibutylamino)-ethyl-L-glutamic acid) (PEG-b-PN4LG) prepared in Example 2 (48 h).

The critical micelle concentration (CMC) of poly(ethylene glycol)-block-poly(2-(dibutylamino)-ethyl-L-glutamic acid) (PEG-b-PN4LG) prepared in Examples 1 to 4 was measured at pH 6.8, 6.9, 7.0 and 7.1 (FIG. 8).

As the result of the test, in the block copolymer of the present disclosure, it was verified that stable micelles were formed at pH 7.4, and no micelles were formed at pH 7.0 (FIG. 8). This means that the copolymer cannot form micelles at a low pH (pH 7.0 or lower) since the whole PNLG becomes soluble due to the increase of ionization of the tertiary amine present in PNLG, and at pH 7.4, micelles due to self-assembly are formed since hydrophobicity is shown due to the decrease of ionization of PNLG. The measured critical micelle concentration values are shown in the following Table 3.

Test Example 2-5

Size Measurement of pH-Sensitive Copolymer

The size of poly(ethylene glycol)-block-poly(2-(dibutylamino)-ethyl-L-glutamic acid) (PEG-b-PNLG) prepared in Examples 1 to 4 was measured at pH 7.4 using a dynamic light scattering (DIS) method. The measured diameter values of the micelles are shown in the following Table 3.

TABLE 3

|  | Polymer Type | Mn | pKb | CMC (mg/mL) | Size (pH 7.4) |
|---|---|---|---|---|---|
| Preparation Example 1 | PEG-b-PBLG | 11,570 | — | — | — |
| Preparation Example 2 | PEG-b-PBLG | 13,541 | — | — | — |
| Preparation Example 3 | PEG-b-PBLG | 17,045 | — | — | — |
| Comparative Example 1 | PEG-b-PN4LG | 11,115 | — | — | — |
| Comparative Example 2 | PEG-b-PN4LG | 11,216 | — | — | — |
| Example 1 | PEG-b-PN4LG | 12,823 | 6.32 | 0.020 | 46.0 nm |
| Example 2 | PEG-b-PN4LG | 13,942 | 6.55 | 0.019 | 45.2 nm |
| Example 3 | PEG-b-PN4LG | 12,340 | 6.65 | 0.019 | 42.0 nm |
| Example 4 | PEG-b-PN4LG | 12,011 | 6.69 | 0.017 | 40.0 nm |
| Example 5 | PEG-b-PN3LG | 12,959 | 8.30 | — | — |
| Example 6 | PEG-b-PNLG | 14,000 |  |  |  |

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

The invention claimed is:

1. A peptide based block copolymer represented by the following Chemical Formula 1:

[Chemical Formula 1]

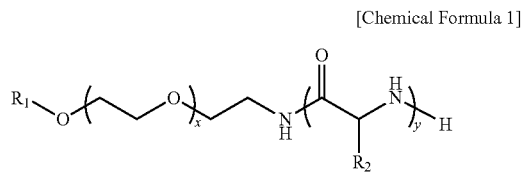

wherein,
X is an integer of 10 to 200;
Y is an integer of 50 to 100;
$R_1$ is hydrogen or $C_{1-4}$ alkyl;
$R_2$s are each independently i)

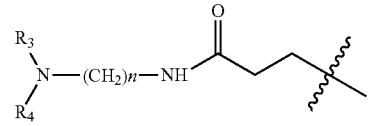

(substituent A) or

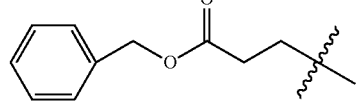

(substituent B), or ii)

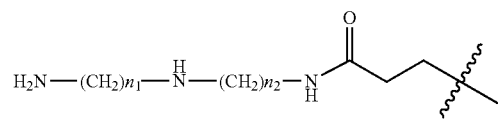

(substituent C) or

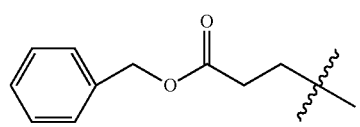 [SMILES: *CCC(=O)OCc1ccccc1]

(substituent B),
wherein, 80% or more of y number of $R_2$s are i) the substituent A, or ii) the substituent C; and
the above $R_3$ and $R_4$ are $C_{1-6}$ alkyl, the n is an integer of 1 to 6, and the $n_1$ and $n_2$ are each independently integers of 1 to 6.

2. The block copolymer of claim 1, wherein 88% or more of y number of $R_2$s are the substituent A.

3. The block copolymer of claim 1, wherein 93% or more of y number of $R_2$s are the substituent A.

4. The block copolymer of claim 1, wherein 96% or more of y number of $R_2$s are the substituent A.

5. The block copolymer of claim 1, wherein $R_1$ is methyl in the Chemical Formula 1.

6. The block copolymer of claim 1, wherein $R_3$ and $R_4$ are isopropyl or n-butyl in the Chemical Formula 1.

7. The block copolymer of claim 1, wherein n is 2 in the Chemical Formula 1.

8. The block copolymer of claim 1, wherein $n_1$ and $n_2$ are 2 in the Chemical Formula 1.

9. A polymer micelle-type drug composition comprising:
(a) the block copolymer of claim 1; and
(b) a molecular imaging marker, a contrast medium or a therapeutic material, which are included inside the block copolymer.

10. A method for preparing the block copolymer of claim 1 comprising:
preparing a compound of the following Chemical Formula 2 by reacting glutamic acid, benzyl ester and triphosgene (Step 1);
preparing a compound of the following Chemical Formula 4 by copolymerizing the compound of the following Chemical Formula 2 with a compound of the following Chemical Formula 3 (Step 2); and
reacting the compound of the following Chemical Formula 4 with a compound of the following Chemical Formula 5 or a compound of the following Chemical Formula 6 (Step 3)

[Chemical Formula 2]

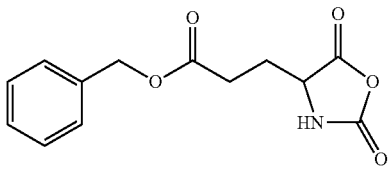

[Chemical Formula 3]

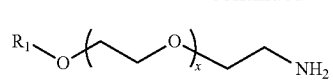

[Chemical Formula 4]

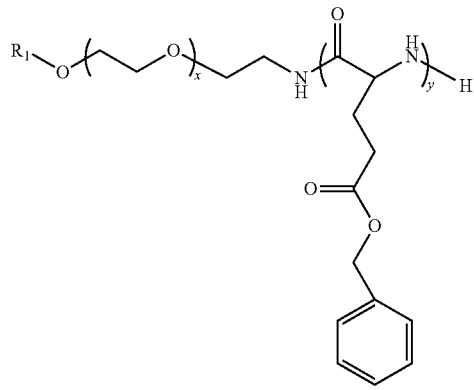

[Chemical Formula 5]

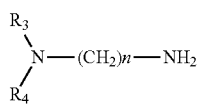

[Chemical Formula 6]

$H_2N-(CH_2)n_1-\overset{H}{N}-(CH_2)n_2-NH_2$ wherein, in the formulae, x, y, $R_1$, $R_3$, $R_4$, n, $n_1$ and $n_2$ are the same as those defined in claim 1.

11. The method for preparing the block copolymer of claim 10, wherein the reaction time ranges from 36 hours to 72 hours in the Step 3.

* * * * *